United States Patent [19]

Isogai et al.

[11] 4,404,394

[45] Sep. 13, 1983

[54] PROCESS FOR PRODUCING ADIPIC ACID DIESTER

[75] Inventors: Nobuo Isogai; Motoyuki Hosokawa; Takashi Okawa; Natsuko Wakui; Toshiyasu Watanabe, all of Niigata, Japan

[73] Assignee: Mitsubishi Gas Chemical Company, Inc., Tokyo, Japan

[21] Appl. No.: 318,980

[22] Filed: Nov. 6, 1981

[30] Foreign Application Priority Data

Nov. 25, 1980 [JP] Japan .............................. 55-165718

[51] Int. Cl.$^3$ ............................................. C07C 67/38
[52] U.S. Cl. .................................. 560/204; 560/190; 560/206
[58] Field of Search .................... 560/204, 206, 190

[56] References Cited

U.S. PATENT DOCUMENTS 4,138,580  2/1979  Umemara et al. ................. 560/204
4,169,956 10/1979  Kummer et al. .................... 560/204
4,171,451 10/1979  Kummer et al. .................... 560/204
4,256,909  3/1981  Kummer et al. .................... 560/204
4,258,203  3/1981  Kummer et al. .................... 560/204
4,259,519  3/1981  Stille ................................... 560/193
4,259,520  3/1981  Kummer et al. .................... 560/204

Primary Examiner—Natalie Trousof
Assistant Examiner—Vera C. Clarke
Attorney, Agent, or Firm—Browdy & Neimark

[57] ABSTRACT

A process for producing adipic acid diester which comprises the first step of reacting butadiene, carbon monoxide and an alcohol in the present of cobalt carbonyl catalyst at a temperature of from 80° to 160° C. to form a 3-pentenoic acid ester, and
the second step of reacting the 3-pentenoic acid ester in the reaction mixture, carbon monoxide and an alcohol at a temperature of from 160° to 220° C., characterized in that the first and second reactions are carried out in an amine solvent is disclosed.

6 Claims, No Drawings

PROCESS FOR PRODUCING ADIPIC ACID DIESTER

BACKGROUND OF THE INVENTION

This invention relates to a process for producing an adipic acid diester which comprises reacting butadiene, carbon monoxide and an alcohol in the presence of cobalt carbonyl catalyst and a specific reaction medium.

Processes for producing an adipic acid diester by reacting butadiene, carbon monoxide and an alcohol in the presence of cobalt carbonyl catalyst have been known in the prior art.

For example, Japanese Patent Publication No. 20177/1974 discloses a process for producing an adipic acid diester from butadiene, carbon monoxide an an alcohol which comprises the first step of reacting butadiene, carbon monoxide an an alcohol in the presence of cobalt carbonyl catalyst and pyridine at a temperature of 120°–160° C. to form a 3-pentenoic acid ester, and the second step of reacting the resulting 3-pentenoic acid ester in the reaction mixture, carbon monoxide and an alcohol at a temperature of 160°–180° C. without separating the 3-pentenoic acid ester, cobalt carbonyl catalyst and pyridine.

Patent Publication No. 20177/1974 also discloses the process which comprises the first step of reacting butadiene, carbon monoxide and an alcohol in the presence of cobalt carbonyl catalyst and pyridine at a temperature of 120°–160° C. to form a 3-pentenoic acid ester, and the second step of separating the resulting 3-pentenoic acid ester from the reaction mixture, and reacting the 3-pentenoic acid ester, carbon monoxide and an alcohol in the presence of cobalt carbonyl catalyst and pyridine at a temperature of 160°–200° C.

However, in Patent Publication No. 20177/1974, the yield of object product in the former method in which the second step is carried out without separating the 3-pentenoic acid ester, which is the reaction product in the first step, from the reaction mixture is inferior to that in the latter method in which after the 3-pentenoic acid ester, which is the reaction product in the first step, is separated from the reaction mixture before carrying out the second step reaction.

Therefore, in order to obtain an adipic acid diester in a high yield according to the invention of Patent Publication No. 20177/1974, it is necessary to separate from the reaction mixture the 3-pentenoic acid ester obtained through the hydroesterification reaction of butadiene and transfer it to another reactor, and the 3-pentenoic acid ester is hydroesterified in the another reactor. However, such process is complicated and the yield of object product in the process is not completely satisfactory. In addition, the reaction rate in the hydroesterification reaction of butadiene in the presence of pyridine solvent alone is low, so a large amount of expensive cobalt carbonyl catalyst has to be used in order to increase the reaction rate and recovery of the catalyst is costly.

SUMMARY OF THE INVENTION

The present inventors carried out research on a process for producing an adipic acid diester by hydroesterification reaction of butadiene in a high yield and with a high selectivity; that is, research was directed to enhancing the catalyst activity in such process. As a result, we found that when the reaction of butadiene, carbon monoxide and an alcohol are carried out in a specific reaction medium, an adipic acid diester can be produced in high yield by a single process that uses a small amount of a cobalt carbonyl catalyst to achieve adequate hydroesterification rate and wherein 3-pentenoic acid ester is not separated from the hydroesterified solution of butadiene but is immediately subjected to hydroesterification of 3-pentenoic acid ester after changing the reaction temperature.

This invention relates to a process for producing an adipic acid diester which comprises the first step of reacting butadiene, carbon monoxide and an alcohol in the presence of cobalt carbonyl catalyst at a temperature of from 80° to 160° C., to form a 3-pentenoic acid ester, and the second step of reacting the 3-pentenoic acid ester in the reaction mixture, carbon monoxide and an alcohol at a temperature of from 160° to 220° C., characterized in that the first and second reactions are carried out in a reaction medium comprising at least two amine solvents selected from the group consisting of pyridine, guinoline, isoquinoline and substituted pyridine, substituted quinoline and substituted isoquinoline in which substituent or substituents are selected from the group consisting of alkyl having 1–6 carbon atoms, alkenyl having 1–6 carbon atoms, aryl, alkylaryl having 7–10 carbon atoms and aralkyl having 7–10 carbon atoms and optionally at least one solvent selected from the group consisting of hydrocarbons, esters, ethers and mixtures thereof.

DETAILED DESCRIPTION OF THE INVENTION

The amine solvents employed in the present invention include pyridine, quinoline, isoquinoline, α-picoline, β-picoline, γ-picoline, 2,3-lutidine, 2,4-lutidine, 2,5-lutidine, 2,6-lutidine, 3,4-lutidine, 3,5-lutidine, 4-benzyl pyridine, 4-vinyl pyridine, quinoline and isoquinoline. Of these compounds, pyridine, β-picoline, γ-picoline, 3,4-lutidine, 3,5-lutidine and isoquinoline are preferred.

It is critical that at least two of the above mentioned amine solvents be used. In general, any one of the at least two amine solvents is preferably used in an amount of more than 2 moles %, more preferably 5 moles %, most preferably 10 moles % on the basis of total mole of the amine solvents. The case of using at least two amine solvents in which one of the amine solvents is present in an amount of less than 2 moles % gives superior results to the case of using one amine solvent alone, but the use of a mixture of the amine solvents in which any one of the amine solvents is present in an amount of more than 2 moles % gives results superior to those obtained with the use of one amine solvent.

The amount of mixture of the amine solvents employed is not critical. In general, the mixture of the amine solvents is used in an amount of from 0.05 to 10 parts by weight on the basis of 1 part by weight of butadiene, preferably from 0.2 to 3 parts by weight. Use of the mixed amine solvents in an amount less than 0.05 parts by weight is likely to cause side-reaction. Use of the mixed amine solvents in an amount of more than 10 parts by weight suppresses hydroesterification reaction of a 3-pentenoic acid ester.

At least one solvent selected from the group consisting of hydrocarbons, esters and ethers may be used together with the above amine solvents. Hydrocarbon solvents include, for example, hexane, octane, cyclohexane, benzene, toluene and decaline. Ether solvents include, for example, aliphatic ethers, such as diethyl ether, tetrahydrofuran and dioxane. Ester solvents include aliphatic ester, such as methyl acetate.

The amount of the solvent employed is not critical. In general, the solvent is used in an amount of from 0.1 to 10 parts by weight on the basis of 1 part by weight of butadiene, preferably from 0.3 to 3 parts by weight.

The cobalt carbonyl catalyst employed in the present invention include cobalt carbonyl and cobalt carbonyl complex.

The cobalt carbonyl catalyst may be the synthetic solution obtained by reacting synthetic gas (CO and $H_2$) with cobalt compound(s) comprising inorganic cobalt compounds, such as cobalt hydroxide, cobalt carbonate and basic cobalt carbonate or organic cobalt compounds, such as cobalt salt of organic acid, cobaltocene and cobalt acetylacetonate in the alcohol employed as a starting material, or the synthetic solution obtained by reacting synthetic gas (CO and $H_2$) with cobalt compounds in the presence of pyridine, quinoline, isoquinoline, alkyl-substituted pyridine, alkyl-substituted quinoline, alkyl-substituted isoquinoline or other compound having ligand.

In the prior method for producing an adipic acid diester by hydroesterificating butadine and hydroesterificating a 3-pentenoic acid ester by using a large amount of cobalt carbonyl or cobalt carbonyl complex, the cobalt carbonyl or the cobalt carbonyl complex must be prepared in high purity and high yield by a complicated and costly process. On the other hand, since an adipic acid diester can be prepared by using a small amount of catalyst according to the present invention, the synthetic solution containing cobalt carbonyl catalyst can be prepared by a simple method from an inorganic or organic cobalt compound.

The amount of cobalt carbonyl catalyst employed is not critical. When dicobalt octacarbonyl is employed, dicobalt octacarbonyl in an amount of 0.001 to 0.05 moles per 1 mole of butadiene, preferably dicobalt octacarbonyl in an amount of 0.005 to 0.03 moles may be industrially used. The use of catalyst in an amount of less than the lower limit as mentioned above lowers the reaction speed too much. The use of catalyst in an amount of more than the upper limit merely adds to production cost, since the cost of recovering the catalyst increases.

Alcohols employed in the present invention include lower aliphatic alcohols having 1–10 carbon atoms such as methanol, ethanol, propanol and butanol. Methanol is important industrially. One of these alcohols or mixture thereof may be used. The amount of the alcohol employed is not critical. The alcohol in an amount of at least 2 moles per 1 mole of butadiene, preferably the alcohol in an amount of 2 to 10 moles per 1 mole of butadiene may be used. When the alcohol in an amount of less than 2 times of mole to butadiene is used, expensive butadiene is consumed for undesirable side reaction. The use of the alcohol in an amount of more than 10 moles per 1 mole of butadiene lowers the hydroesterification reaction speed of butadiene and a 3-pentenoic acid ester.

The partial pressure of carbon monoxide is not critical in the hydroesterification reaction of butadiene and hydroesterification reaction of a 3-pentenoic acid ester. The partial pressure of carbon monoxide may be more than 50 $Kg/cm^2$, and preferably, the partial pressure is in the range of 100 to 400 $Kg/cm^2$ in the practice of the present invention.

The reaction temperature is in the range of from 80° to 160° C. in the esterification reaction of butadiene, and preferably is in the range of from 100° to 140° C. The reaction temperature is in the range of from 160° to 220° C. in the hydroesterification reaction of a 3-pentenoic acid ester, and preferably is in the range of from 170° to 200° C.

According to the present invention, an adipic acid diester can industrially be produced from butadiene by using a small amount of the catalyst without requiring any complicated operation.

The present invention can be carried out either as batch process or as a continuous process.

The present invention is further illustrated by non-limiting Examples.

EXAMPLES 1–10

Into a 200 ml stainless steel autoclave equipped with magnet stirrer were charged 15 grs. (0.277 moles) of butadiene, 22 grs. (0.686 moles) of methanol and 2 grs. (0.0058 mol) of dicobalt octacarbonyl catalyst and mixed amine solvents as given in Table 1. The reaction was carried out at 130° C. under carbon monoxide partial pressure of 300 $Kg/cm^2$ for 1.5 hours and the reaction was further carried out at 185° C. under carbon monoxide partial pressure of 300 $Kg/cm^2$ for additional 2 hours.

The results are shown in Table 1.

TABLE 1

| | | | | Ex. 1 | Ex. 2 | Ex. 3 | Ex. 4 |
|---|---|---|---|---|---|---|---|
| components | butadiene | | g (mol) | 15 (0.277) | same as Ex. 1 | same as Ex. 1 | same as Ex. 1 |
| | methanol | | g (mol) | 22 (0.686) | | | |
| | $Co_2(CO)_8$ | | g (mol) | 2 (0.0058) | | | |
| | mixed solution of amine | (1) | kind | pyridine | pyridine | β-picoline | pyridine |
| | | | g (mol) | 10 (0.126) | 10 (0.126) | 10 (0.107) | 10 (0.126) |
| | | (2) | kind | isoquinoline | γ-picoline | γ-picoline | isoquinoline |
| | | | g (mol) | 10 (0.077) | 10 (0.107) | 10 (0.107) | 10 (0.077) |
| | hydrocarbon solvent, ether solvent or ester solvent | | kind | | | | hexane |
| | | | g (mol) | | | | 20 (0.232) |
| reaction conditions | hydroesterification of butadiene | reaction pressure of CO kg/cm² | | 300 | same as Ex. 1 | same as Ex. 1 | same as Ex. 1 |
| | | reaction temperature °C. | | 130 | | | |
| | | reaction time Hr | | 1.5 | | | |
| | hydroesterification of 3-pentenoic | reaction pressure of CO kg/cm² | | 300 | same as Ex. 1 | same as Ex. 1 | same as Ex. 1 |
| | | reaction temperature | | 185 | | | |

TABLE 1-continued

|  |  |  |  |  |  |  |
|---|---|---|---|---|---|---|
| ester | °C. |  |  |  |  |  |
|  | reaction time Hr |  | 2.0 |  |  |  |
| conversion of butadiene | mol % | 100 | 100 | 100 | 100 |  |
| selectivity to dimethyl adipate | mol % | 66.4 | 69.7 | 67.1 | 72.5 |  |
| selectivity to methyl 3-pentenoate | mol % | 10.1 | 8.5 | 10.7 | 7.0 |  |
| selectivity to methyl n-valerate | mol % | 4.2 | 8.1 | 6.9 | 4.3 |  |
| selectivity to dimethyl 2-ethyl succinate | mol % | 1.8 | 1.7 | 1.6 | 2.1 |  |
| selectivity to dimethyl 2-methyl glutarate | mol % | 8.2 | 6.8 | 6.0 | 7.9 |  |

|  |  |  |  |  | Ex. 5 | Ex. 6 | Ex. 7 |
|---|---|---|---|---|---|---|---|
| components | butadiene |  |  | g (mol) | 15 (0.277) | same as Ex. 5 | same as Ex. 5 |
|  | methanol |  |  | g (mol) | 22 (0.686) |  |  |
|  | Co$_2$(CO)$_8$ |  |  | g (mol) | 2 (0.0058) |  |  |
|  | mixed | (1) | kind |  | pyridine | pyridine | pyridine |
|  | solution of |  |  | g (mol) | 10 (0.126) | 10 (0.126) | 10 (0.126) |
|  | amine | (2) | kind |  | γ-picoline | β-picoline | β-picoline |
|  |  |  |  | g (mol) | 10 (0.107) | 10 (0.107) | 10 (0.093) |
|  | hydrocarbon solvent, |  | kind |  | benzene | hexane | diethyl ether |
|  | ether solvent or ester solvent |  |  | g (mol) | 20 (0.256) | 20 (0.232) | 20 (0.170) |
| reaction conditions | hydroesterification of butadiene | reaction pressure of CO kg/cm$^2$ |  |  | 300 | same as Ex. 5 | same as Ex. 5 |
|  |  | reaction temperature °C. |  |  | 130 |  |  |
|  |  | reaction time Hr |  |  | 1.5 |  |  |
|  | hydroesterication of 3-pentenoic ester | reaction pressure of CO kg/cm$^2$ |  |  | 300 | same as Ex. 5 | same as Ex. 5 |
|  |  | reaction temperature °C. |  |  | 185 |  |  |
|  |  | reaction time Hr |  |  | 2.0 |  |  |
| conversion of butadiene |  |  |  | mol % | 100 | 100 | 100 |
| selectivity to dimethyl adipate |  |  |  | mol % | 75.4 | 77.5 | 73.1 |
| selectivity to methyl 3-pentenoate |  |  |  | mol % | 4.8 | 4.0 | 7.5 |
| selectivity to methyl n-valerate |  |  |  | mol % | 9.1 | 6.6 | 7.3 |
| selectivity to dimethyl 2-ethyl succinate |  |  |  | mol % | 1.7 | 1.8 | 1.9 |
| selectivity to dimethyl 2-methyl glutarate |  |  |  | mol % | 6.7 | 7.8 | 6.8 |

|  |  |  |  |  | Ex. 8 | Ex. 9 | Ex. 10 |
|---|---|---|---|---|---|---|---|
| components | butadiene |  |  | g (mol) | 15 (0.277) | same as Ex. 8 | same as Ex. 8 |
|  | methanol |  |  | g (mol) | 22 (0.686) |  |  |
|  | Co$_2$(CO)$_8$ |  |  | g (mol) | 2 (0.0058) |  |  |
|  | mixed | (1) | kind |  | pyridine | pyridine | β-picoline |
|  | solution of |  |  | g (mol) | 10 (0.126) | 10 (0.126) | 10 (0.107) |
|  | amine | (2) | kind |  | 3,4-lutidine | 3,5-lutidine | γ-picoline |
|  |  |  |  | g (mol) | 10 (0.093) | 10 (0.093) | 10 (0.107) |
|  | hydrocarbon solvent, |  | kind |  | cyclohexane | decalin | methyl acetate |
|  | ether solvent or ester solvent |  |  | g (mol) | 20 (0.238) | 20 (0.145) | 20 (0.197) |
| reaction conditions | hydroesterification of butadiene | reaction presssure of CO kg/cm$^2$ |  |  | 300 | same as Ex. 8 | same as Ex. 8 |
|  |  | reaction temperature °C. |  |  | 130 |  |  |
|  |  | reaction time Hr |  |  | 1.5 |  |  |
|  | hydroesterication of 3-pentenoic ester | reaction pressure of CO kg/cm$^2$ |  |  | 300 | same as Ex. 8 | same as Ex. 8 |
|  |  | reaction temperature °C. |  |  | 185 |  |  |
|  |  | reaction time Hr |  |  | 2.0 |  |  |
| conversion of butadiene |  |  |  | mol % | 100 | 100 | 100 |
| selectivity to dimethyl adipate |  |  |  | mol % | 69.8 | 67.3 | 70.5 |
| selectivity to methyl 3-pentenoate |  |  |  | mol % | 7.6 | 8.1 | 10.4 |
| selectivity to methyl n-valerate |  |  |  | mol % | 8.7 | 9.3 | 7.2 |
| selectivity to dimethyl 2-ethyl succinate |  |  |  | mol % | 2.0 | 1.9 | 1.6 |
| selectivity to dimethyl 2-methyl glutarate |  |  |  | mol % | 8.0 | 8.2 | 5.7 |

Control Tests 1 and 2

The procedures of the above examples were repeated by using starting materials and reaction conditions as shown in Table 2. The results are shown in Table 2.

TABLE 2

|  |  |  |  | control test 1 | control test 2 |
|---|---|---|---|---|---|
| components | butadiene |  | g (mol) | 15 (0.277) | 15 (0.277) |
|  | methanol |  | g (mol) | 22 (0.686) | 22 (0.686) |
|  | Co$_2$(CO)$_8$ |  | g (mol) | 2 (0.0058) | 2 (0.0058) |
|  | pyridine |  | g (mol) | 20 (0.253) | 20 (0.253) |
|  | benzene |  | g (mol) |  | 20 (0.256) |
| reaction conditions | hydroesterification of | reaction pressure of CO kg/cm$^2$ |  | 300 | 300 |

TABLE 2-continued

|  |  |  | control test 1 | control test 2 |
|---|---|---|---|---|
| butadiene | reaction temperature °C. | | 130 | 130 |
|  | reaction time Hr | | 1.5 | 1.5 |
| hydroesterification of 3-pentenoic ester | reaction pressure of CO kg/cm$^2$ | | 300 | 300 |
|  | reaction temperature °C. | | 185 | 185 |
|  | reaction time Hr | | 2 | 2 |
| conversion of butadiene | | mol % | 94 | 97.8 |
| selectivity to dimethyl adipate | | mol % | 42 | 48 |
| selectivity to methyl 3-pentenoate | | mol % | 6.2 | 2.2 |
| selectivity to methyl n-valerate | | mol % | 5.1 | 5.3 |
| selectivity to dimethyl 2-ethyl succinate | | mol % | 1.6 | 1.5 |
| selectivtiy to dimethyl 2-methyl glutarate | | mol % | 8.1 | 7.6 |

What is claimed is:

1. A process for producing an adipic acid diester which comprises:

the first step of reacting butadiene, carbon monoxide and an alcohol in the presence of a cobalt carbonyl catalyst and amine solvents at a temperature of from 80° to 160° C. to form a 3-pentenoic acid ester, the amount of the alcohol employed being more than 2 moles per 1 mole of butadiene, and the amount of the solvents employed being in the range of 0.05 to 10 parts by weight per 1 part by weight of butadiene; and the second step of reacting the 3-pentenoic acid ester in the reacting mixture of the first step, carbon monoxide and the unreacted alcohol in the presence of the catalyst and the solvents at a temperature of from 160° to 220° C., said 3-pentenoic acid ester being subjected to the reaction of the second step without being separated from the reaction mixture, wherein the amine solvents comprise at least two amine solvents selected from the group consisting of pyridine, quinoline, isoquinoline, substituted pyridine, substituted quinoline and substituted isoquinoline in which any substituent or substituents are selected from the group consisting of alkyl having 1-6 carbon atoms, alkenyl having 1-6 carbon atoms, aryl, alkaryl having 7-10 carbon atoms and aralkyl having 7-10 carbon atoms.

2. The process as defined in claim 1 wherein the reaction medium further contains at least one solvent selected from the group consisting of hydrocarbons, ethers and esters.

3. The process as defined in claim 1 wherein any one of at least two solvents is present in an amount of more than 2 moles % on the basis of total mole of the amine solvents.

4. The process as defined in claim 1 wherein the cobalt carbonyl catalyst is dicobalt octacarbonyl.

5. The process as defined in claim 4 wherein dicobalt octacarbonyl is used in an amount ranging from 0.001 to 0.05 moles per 1 mole of butadiene.

6. The process as defined in claim 1 wherein the partial pressure of carbon monoxide is more than 50 Kg/cm$^2$.

* * * * *